United States Patent
Lanver et al.

(10) Patent No.: US 8,686,193 B2
(45) Date of Patent: Apr. 1, 2014

(54) METHOD FOR PRODUCING M-SUBSTITUTED PHENYLALKANOLS BY MEANS OF ISOMERIZATION

(75) Inventors: Andreas Lanver, Mannheim (DE); Klaus Ebel, Lampertheim (DE); Karl Beck, Östringen (DE); Ralf Pelzer, Fürstenberg (DE); Jörg Botzem, Limburgerhof (DE); Ulrich Griesbach, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/503,488

(22) PCT Filed: Oct. 19, 2010

(86) PCT No.: PCT/EP2010/065673
§ 371 (c)(1),
(2), (4) Date: Apr. 23, 2012

(87) PCT Pub. No.: WO2011/048068
PCT Pub. Date: Apr. 28, 2011

(65) Prior Publication Data
US 2012/0209031 A1     Aug. 16, 2012

(30) Foreign Application Priority Data
Oct. 23, 2009   (EP) ..................... 09173907

(51) Int. Cl.
*C07C 45/51*    (2006.01)
*C07C 29/56*    (2006.01)
*C07C 47/22*    (2006.01)
*A61K 8/18*     (2006.01)

(52) U.S. Cl.
USPC .............. 568/425; 568/427; 568/715; 512/27

(58) Field of Classification Search
USPC ............... 568/425, 427, 715; 512/27
See application file for complete search history.

(56) References Cited

U.S. PATENT DOCUMENTS

| 6,013,618 A * | 1/2000 | Morelli et al. ............... 512/1 |
| 2011/0118510 A1 | 5/2011 | Weis et al. |
| 2012/0209030 A1 | 8/2012 | Lanver et al. |

FOREIGN PATENT DOCUMENTS

| DE | 2952719 A1 | 7/1981 |
| EP | 0045571 A1 | 2/1982 |
| JP | 2009830 A | 1/1990 |
| JP | 2238097 A | 9/1990 |
| WO | WO-2008/053148 A1 | 5/2008 |

OTHER PUBLICATIONS

International Search Report for PCT/EP2010/065673 mailed May 20, 2011.

* cited by examiner

*Primary Examiner* — Sikarl Witherspoon
(74) *Attorney, Agent, or Firm* — Novak Druce Connolly Bove + Quigg LLP

(57) ABSTRACT

The invention relates to a process for the preparation of m-substituted phenylalkanols of the formula (I)

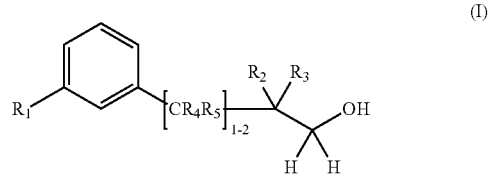

in which $R_1$ is $C_1$-$C_5$-alkyl and $R_2$, $R_3$, $R_4$ and $R_5$, independently of one another, are hydrogen or methyl, wherein a p-substituted phenylalkanol of the formula (II)

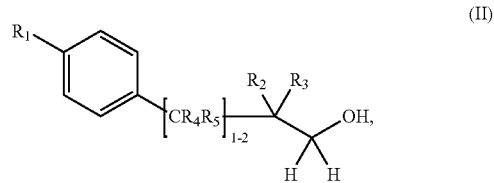

in which $R_1$, $R_2$, $R_3$, $R_4$ and $R_5$ having the meanings given under formula (I), is isomerized in the presence of a Friedel-Crafts catalyst to give an m-substituted phenylalkanol of the formula (I). From the m-substituted phenylalkanols of the formula (I) it is possible to form, by oxidation or dehydrogenation, as products of value, the corresponding aldehydes, which are known as fragrances and aroma chemicals.

17 Claims, No Drawings

METHOD FOR PRODUCING M-SUBSTITUTED PHENYLALKANOLS BY MEANS OF ISOMERIZATION

RELATED APPLICATIONS

This application is a national stage application (under 35 U.S.C. §371) of PCT/EP2010/065673, filed Oct. 19, 2010, which claims benefit of European Patent Application No. 09173907.8, filed Oct. 23, 2009.

The present invention relates to a process for the preparation of m-substituted phenylalkanols by isomerization of p-substituted phenylalkanols. The m-substituted phenylalkanols and also the m-substituted phenylalkanals prepared from these, for example derivatives of the odorant 3-phenyl-1-propanol, are of interest as aroma chemicals.

Various syntheses are known for preparing m-substituted phenylalkanols. WO 2008/053148 describes a 3-stage synthesis for preparing 3-(3-tert-butylphenyl)-propanal starting from 1-tert-butyl-3-ethylbenzene. Here, the starting compound is firstly brominated to give 1-tert-butyl-3-(1-bromoethyl)benzene and then eliminated to give the corresponding substituted styrene. Hydroformylation then gives 3-(3-tert-butylphenyl)propanal. This synthesis would appear not to be very suitable for an industrial process on account of low yields.

The preparation of 2-methyl-3-(3-tert-butylphenyl)propanal and of 2-methyl-3-(3-isobutylphenyl)propanal is achieved by Ishii et al. (J. Org. Chem. 2005, 70, 5471-5474) through palladium-catalyzed oxidative coupling of tert-butylbenzene or isopropyl-benzene with methacrolein followed by a palladium-catalyzed hydrogenation. In the coupling step, a catalyst system consisting of $Pd(OAc)_2$ and $H_4PMo_{11}VO_{40} \times 26H_2O$ is used. A large amount of catalyst of ca. 7 mol % is required. At a yield of ca. 65%, the m/p ratio is 56/44 (for 2-methyl-3-(3-tert-butylphenyl)propanal) and 51/40 (for 2-methyl-3-(3-isobutylphenyl)propanal). This process too would also appear not to be very suitable for an industrial process, since the amount of the expensive catalyst used is large and the selectivity to give the m-isomer is low.

EP 0 045 571 describes the Friedel-Crafts alkylation of 2-methyl-3-phenylpropanol to give 2-methyl-3-(3-tert-butylphenyl)propanol and 2-methyl-3-(4-tert-butylphenyl)-propanol. The alkylating reagents used are isobutylene, diisobutylene and tert-butyl chloride. The catalysts used are iron chloride and phosphoric acid and the solvents used are methylene chloride or phosphoric acid. Depending on the reaction conditions and the catalyst, m/p ratios of 1/13 to 1/5 are obtained. The overall yields (m-isomer and p-isomer) are up to 52%.

DE 29 52 719 likewise describes the iron chloride-catalyzed Friedel-Crafts alkylation of 2-methyl-3-phenylpropanol. In cyclohexane or dichloroethane as solvent, a yield of 84-86% of 2-methyl-3-(4-tert-butylphenyl)propanol was obtained. The formation of the m-isomeric compound (2-methyl-3-(3-tert-butylphenyl)propanol), was not demonstrated. A disadvantage of the described Friedel-Crafts alkylations is the small amount of the m-isomeric compound formed (m:p ratio is max. 1:5).

By contrast, the process according to the invention allows the m-substituted phenylalkanols, which serve as precursor for the very interesting correspondingly substituted phenylalkanals, to be prepared in the simplest cost-effective way and in good yield.

The present invention relates to a process for the preparation of phenylalkanols substituted in the m-position which can be obtained by isomerization of phenylalkanols substituted in the p-position. The isomerization takes place over certain Friedel-Crafts catalysts. The invention therefore provides a process for the preparation of m-substituted phenylalkanols of the formula (I)

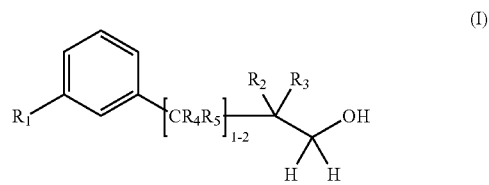

(I)

in which $R_1$ is $C_1$-$C_5$-alkyl and $R_2$, $R_3$, $R_4$ and $R_5$, independently of one another, are hydrogen or methyl, wherein a p-substituted phenylalkanol of the formula (II)

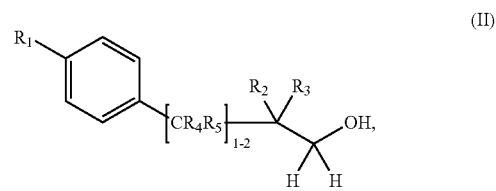

(II)

in which $R_1$, $R_2$, $R_3$, $R_4$ and $R_5$ have the meanings given under formula (I), is isomerized in the presence of a Friedel-Crafts catalyst to give an m-substituted phenylalkanol of the formula (I).

Surprisingly, it has been found that in the isomerization reaction of p-substituted phenylalkanols to give m-substituted phenylalkanols under certain conditions m/p isomer ratios of >1/1 can be obtained.

Suitable alkyl radicals $R_1$ are, for example: methyl, ethyl, n-propyl, isopropyl, n-butyl, isobutyl, sec-butyl, tert-butyl, n-pentyl. Preferred alkyl radicals $R_1$ are: ethyl, isopropyl, isobutyl and tert-butyl.

Preference is given to a process for the preparation of m-substituted phenylpropanols of the formula (III)

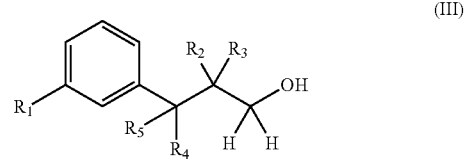

(III)

in which $R_1$, $R_2$, $R_3$, $R_4$ and $R_5$ have the meanings given under formula (I), wherein a p-substituted phenylpropanol of the formula (IV)

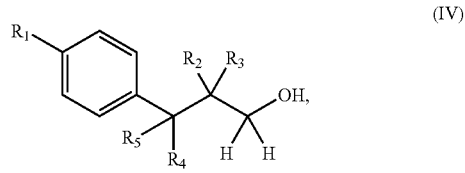

(IV)

in which $R_1$, $R_2$, $R_3$, $R_4$ and $R_5$ have the meanings given under formula (I), is isomerized in the presence of a Friedel-Crafts catalyst to give an m-substituted phenylalkanol of the formula (III). Preferably, $R_1$ is ethyl, isopropyl, isobutyl or tert-butyl.

Particular preference is given to a process wherein the starting material used is a p-substituted phenylpropanol of the formula (V)

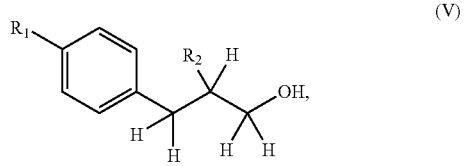

(V)

in which $R_1$ and $R_2$ have the meanings given under formula (I). Preferably, $R_1$ is ethyl, isopropyl, isobutyl or tert-butyl.

A very particularly preferred process is one in which, as starting compound, 2-methyl-3-(4-tert-butylphenyl)propanol is isomerized in the presence of a Friedel-Crafts catalyst, in particular in the presence of aluminum trichloride ($AlCl_3$), to give 2-methyl-3-(3-tert-butylphenyl)propanol.

A likewise particularly preferred process is one in which the starting compound used is 2-methyl-3-(4-isobutylphenyl) propanol, 3-(4-tert-butylphenyl)propanol, 2-methyl-3-(4-isopropylphenyl)propanol, 3-(4-ethylphenyl)-2,2-dimethylpropanol or 3-(4-isopropylphenyl)butanol, and the isomerization is carried out in the presence of a Friedel-Crafts catalyst to give the compounds 2-methyl-3-(3-isobutylphenyl)propanol, 3-(3-tert-butylphenyl)propanol, 2-methyl-3-(3-isopropylphenyl)propanol, 3-(3-ethylphenyl)-2,2-dimethylpropanol or 3-(3-isopropylphenyl)butanol.

Typical Friedel-Crafts catalysts can be used as catalysts. Examples which may be mentioned are $AlCl_3$, $AlBr_3$, $TiCl_4$, $ZrCl_4$, $VCl_3$, $ZnCl_2$, $FeBr_3$ and $FeCl_3$. Preference is given to using the Friedel-Crafts catalysts $AlCl_3$ or $AlBr_3$. In general, the amounts of catalyst used are from 1 to 200 mol %, based on the molar amount of the p-substituted phenylalkanol compound used. Preference is given to amounts of catalysts of from 33% to 110 mol %, based on the molar amount of the p-substituted phenylalkanol compound used.

The isomerization takes place at temperatures between 0° C. and 100° C. Particular preference is given to temperatures between 10° C. and 50° C. The reaction times are 30 minutes to 24 hours. Particular preference is given to reaction times between 1 hour and 6 hours.

The reaction can be carried out solvent-free or in a solvent. Suitable solvents are: cyclohexane, toluene, p-tert-butyltoluene, dichloromethane, 1,2-dichloroethane, chlorobenzene, dichlorobenzene. Particular preference is given to dichloromethane and chlorobenzene.

Preferred starting materials for the isomerization are the following substrates: 2-methyl-3-(4-tert-butylphenyl)propanol, 2-methyl-3-(4-iso-butylphenyl)propanol, 3-(4-tert-butylphenyl)propanol, 2-methyl-3-(4-isopropylphenyl)propanol, 3-(4-ethylphenyl)-2,2-dimethylpropanol, 3-(4-isopropylphenyl)butanol. These give the following m-isomers as main products (in a yield of >25%, with an m/p isomer ratio >1/1) of the reaction: 2-methyl-3-(3-tert-butylphenyl)propanol, 2-methyl-3-(3-iso-butylphenyl)propanol, 3-(3-tert-butylphenyl)propanol, 2-methyl-3-(3-isopropylphenyl)propanol and 3-(3-ethylphenyl)-2,2-dimethylpropanol, 3-(3-isopropylphenyl)butanol. Particular preference is given to the substrate 2-methyl-3-(4-tert-butylphenyl)propanol.

The reaction is generally carried out in such a way that the catalyst is introduced into the phenylalkanol dissolved in the solvent. The work-up takes place by work-up with water, preferably in the presence of alkali, such that an alkaline pH is established, very particularly, preferably in the presence of alkali metal hydroxide solution, such as e.g. sodium hydroxide solution and/or potassium hydroxide solution, and also by distillation of the solvent. Purification of the crude product and isolation of the m-substituted phenylalkanols generally takes place by distillation.

The phenylalkanols mono- and tri-substituted on the aromatic that are formed during the reaction and of the formulae

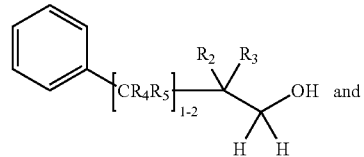

(Ia)

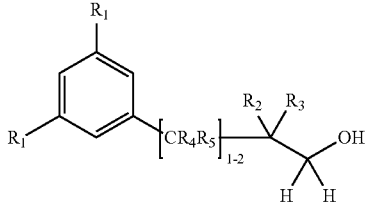

(Ib)

in which $R_1$, $R_2$, $R_3$, $R_4$ and $R_5$ have the meanings given under formula (I) are by-products which can be returned to the isomerization reaction. As a result of returning these products to the reaction mass, the equilibrium between the p-substituted and the m-substituted component and the mono- and tri-substituted phenylalkanols is newly established time after time, as a result of which an increased fraction of the desired m-substituted product is obtained, since this is removed from the reaction mass prior to each return (following work-up and distillation).

The alkanols of the formula (I) prepared according to the invention can be converted to the corresponding aldehydes based on dehydrogenation or oxidation methods known per se (cf. e.g.: Houben-Weyl "Methoden der organischen Chemie" ["Methods of organic chemistry"], Volume 7/1, p. 160 ff, p. 171f). Particularly interesting compounds of this substance class are 2-methyl-3-(3-tert-butylphenyl)propanal, 2-methyl-3-(3-iso-butylphenyl)propanal, 3-(3-tert-butylphenyl)propanal, 2-methyl-3-(3-isopropylphenyl)-propanal, 3-(3-ethylphenyl)-2,2-dimethylpropanal and 3-(3-isopropylphenyl)butanal.

As described in EP-A-0 045 571, phenylpropanols can be converted to the corresponding phenylpropanals by oxidation or dehydrogenation. This reaction is achieved, for example, by copper chromite-catalyzed liquid-phase dehydrogenation.

Preferred starting materials for this conversion to the aldehyde are 2-methyl-3-(3-tert-butylphenyl)propanol, 2-methyl-3-(3-isobutylphenyl)propanol, 3-(3-tert-butylphenyl)-propanol, 2-methyl-3-(3-isopropylphenyl)propanol, 3-(3-ethylphenyl)-2,2-dimethyl-propanol, 3-(3-isopropylphenyl)butanol. These produce the following aldehydes: 2-methyl-3-(3-tert-butylphenyl)propanal, 2-methyl-3-(3-isobutylphenyl)propanal, 3-(3-tert-butylphenyl)propanal, 2-methyl-3-(3-isopropylphenyl)propanal, 3-(3-ethylphenyl)-2,2-dimethylpropanal, 3-(3-isopropylphenyl)butanal.

The invention thus further provides the preparation of the products of value of the formula (VI), which are known as fragrances and aroma chemicals, obtainable from the m-substituted phenylalkanols of the formula (I) by oxidation or dehydrogenation,

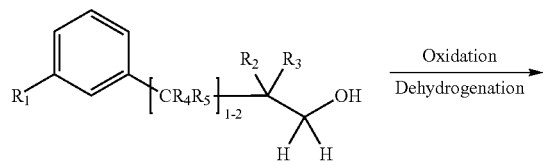

Formula (I)

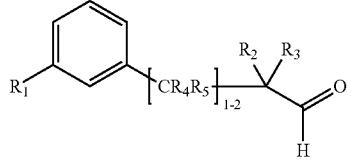

Formula (VI)

in which $R_1$, $R_2$, $R_3$, $R_4$ and $R_5$ have the meanings given under formula (I).

The process according to the invention for the preparation of fragrances of the formula (VI)

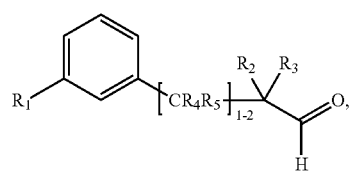
(VI)

in which $R_1$ is $C_1$-$C_5$-alkyl and $R_2$, $R_3$, $R_4$ and $R_5$, independently of one another, are hydrogen or methyl, is notable for the fact that a p-substituted phenylalkanol of the formula (II)

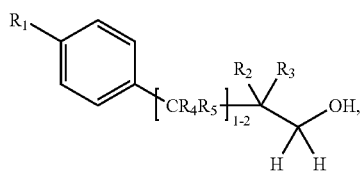
(II)

in which $R_1$, $R_2$, $R_3$, $R_4$ and $R_5$ have the meanings given under formula (I) is isomerized in the presence of a Friedel-Crafts catalyst to give an m-substituted phenylpropanol of the formula (I)

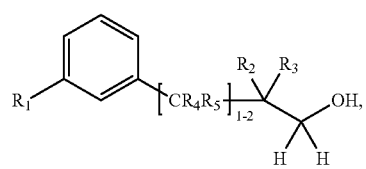
(I)

in which $R_1$, $R_2$, $R_3$, $R_4$ and $R_5$ have the meanings given under formula (I), and then the resulting m-substituted phenylalkanol of the formula (I) is converted to the m-substituted phenylalkanal of the formula (VI) by oxidation or dehydrogenation.

The aldehydes of the formula (VI) obtained according to the process are in part known and in part novel fragrances and aroma substances. A novel fragrance and aroma substance corresponds to the formula (VII)

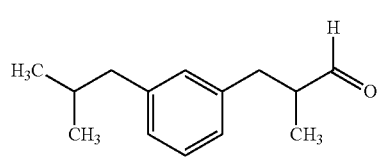
(VII)

and is a further subject matter of the present invention.

Surprisingly, it has also been found that toxicologically advantageous formulations can be prepared by combining one or more of the aldehydes of the formula (VI) obtained according to the process according to the invention together with other aroma chemicals. A further subject matter of the present invention is thus formulations which comprise at least one aldehyde of the formula (VI), in particular the aldehyde of the formula (VIII)

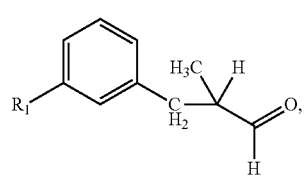
(VIII)

in which $R_1$ is tert-butyl. These formulations are advantageous when they comprise 0 to 1000 ppm of the aldehyde of the formula (IX)

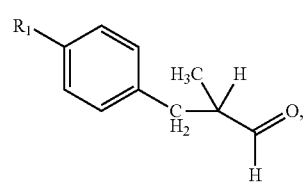
(IX)

in which $R_1$ is tert-butyl.

Formulations which comprise 0 ppm of the aldehyde of the formula (IX) are particularly advantageous.

Besides the m-substituted aldehydes of the formula (VI), in particular besides the m-substituted aldehyde of the formula (VIII), these formulations can comprise one or more of the following aroma chemicals:

a) Menthol of the formula

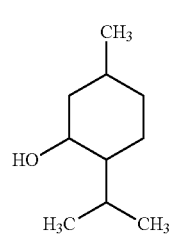
(X)

b) Tonalide of the formula
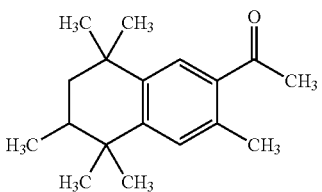
(XI)
c) Iso E Super® of the formula
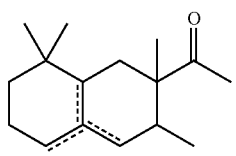
(XII)
d) Galaxolide of the formula
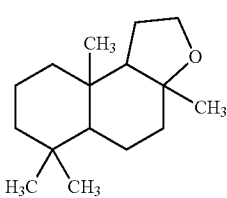
(XIII)
e) Ambroxide of the formula
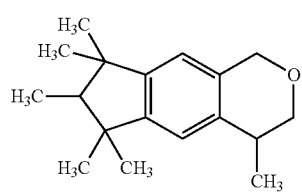
(XIV)
f) Citral, mixture of the stereoisomers of the formulae
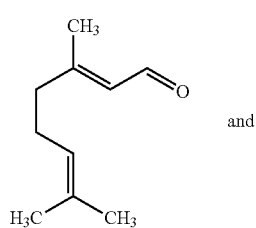
(XV)
and
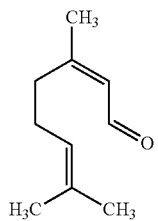
(XVI)
g) Linalool, mixture of the enantiomers of the formulae
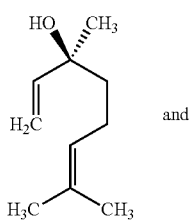
(XVII)
and
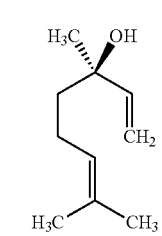
(XVIII)
h) Geraniol of the formula
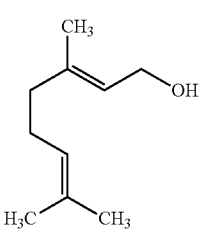
(XIX)
i) Methylionone of the formula
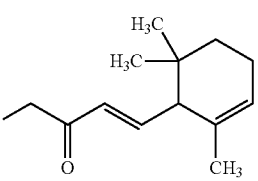
(XX)
j) 2-Phenylethyl alcohol of the formula
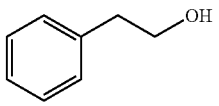
(XXI)

k) Hedione of the formula

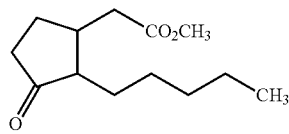

l) Dihydromyrcenol of the formula

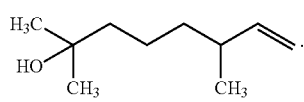

The formulations according to the invention which comprise the aldehydes of the formula (VI) prepared according to the invention, in particular the aldehyde of the formula (VIII) and at least one aroma chemical of the formulae (X) to (XXIII), are valuable formulations which are distinguished by advantageous toxicological properties.

The invention is illustrated in more detail by the examples below. In the examples, all data in % are understood as meaning mol %.

EXAMPLES

Example 1

327 g (1.50 mol) of 2-methyl-3-(4-tert-butylphenyl)propanol were introduced as initial charge in 500 g of dichloromethane. Over the course of 4 h, 220 g (1.65 mol) of $AlCl_3$ were added in portions at room temperature. The mixture was stirred for a further 60 minutes at room temperature. For the work-up, the reaction mixture was slowly added to 1050 g of ice-water. The mixture was heated to room temperature and 670 g of 50% strength sodium hydroxide solution were added. The phases were separated and the organic phase was washed with water (2×200 ml). The solvent was distilled off and the crude product was subjected to fractional distillation at 1 mbar. This gave 104 g of 2-methyl-3-(3-tert-butylphenyl)propanol (33%), 81 g of 2-methyl-3-(4-tert-butylphenyl)propanol (26%). The by-products obtained were 2-methyl-3-phenyl-propanol and 3-(3,5-di-tert-butylphenyl)-2-methylpropanol (together ca. 35%).

Example 2

2.1 g of a mixture consisting of 2-methyl-3-(3-tert-butylphenyl)propanol (30%), 2-methyl-3-(4-tert-butylphenyl)propanol (48%) and 3-(3,5-di-tert-butylphenyl)-2-methylpropanol (18%) were admixed with 2.1 g of 2-methyl-3-phenylpropanol and 6.3 g of dichloromethane. 2.9 g of $AlCl_3$ were added in portions at room temperature. After the mixture had been stirred for 7 hours at room temperature, the mixture was worked-up with water and sodium hydroxide solution and the solvent was removed. This gave a mixture with the following composition: 2-methyl-3-(3-tert-butylphenyl)propanol (34%); 2-methyl-3-(4-tert-butylphenyl)propanol (21%); 3-(3,5-di-tert-butylphenyl)-2-methyl-propanol (5%); 2-methyl-3-phenylpropanol (37%).

Example 3

2.1 g of a mixture consisting of 2-methyl-3-(3-tert-butylphenyl)propanol (30%), 2-methyl-3-(4-tert-butylphenyl) propanol (48%) and 3-(3,5-di-tert-butylphenyl)-2-methylpropanol (18%) were admixed with 2.1 g of 2-methyl-3-phenylpropanol and 6.5 g of 4-tert-butyltoluene. 2.9 g of $AlCl_3$ were added in portions at room temperature. After the mixture had been stirred for 7 hours at room temperature, it was worked-up with water and sodium hydroxide solution, and the solvent was removed. This gave a mixture with the following composition: 2-methyl-3-(3-tert-butylphenyl)propanol (38%); 2-methyl-3-(4-tert-butylphenyl)propanol (23%); 3-(3,5-di-tert-butylphenyl)-2-methylpropanol (17%); 2-methyl-3-phenylpropanol (12%).

Example 4

2.1 g of a mixture consisting of 2-methyl-3-(3-tert-butylphenyl)propanol (30%), 2-methyl-3-(4-tert-butylphenyl) propanol (48%) and 3-(3,5-di-tert-butylphenyl)-2-methylpropanol (18%) were admixed with 2.1 g of 2-methyl-3-phenylpropanol. 2.9 g of $AlCl_3$ were added in portions at room temperature. After the mixture had been stirred for 7 hours at room temperature, it was worked-up with water and sodium hydroxide solution. This gave a mixture with the following composition: 2-methyl-3-(3-tert-butyl phenyl)propanol (31%); 2-methyl-3-(4-tert-butylphenyl)propanol (17%); 3-(3,5-di-tert-butylphenyl)-2-methylpropanol (5%); 2-methyl-3-phenylpropanol (32%).

The invention claimed is:

1. A process for the preparation of an m-substituted phenylalkanol of the formula (I)

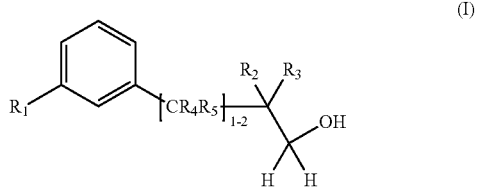

in which $R_1$ is $C_1$-$C_5$-alkyl and $R_2$, $R_3$, $R_4$ and $R_5$, independently of one another, are hydrogen or methyl, wherein a p-substituted phenylalkanol of the formula (II)

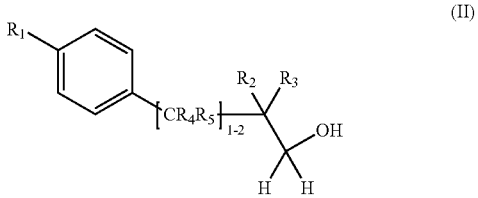

in which $R_1$, $R_2$, $R_3$, $R_4$ and $R_5$ have the meanings given under formula (I), is isomerized in the presence of a Friedel-Crafts catalyst to give the m-substituted phenylalkanol of the formula (I).

2. The process according to claim 1 for the preparation of an m-substituted phenylpropanol of the formula (III)

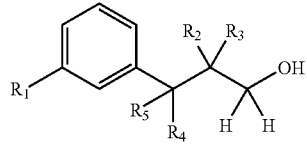
(III)

in which $R_1$ is $C_1$-$C_5$-alkyl and $R_2$, $R_3$, $R_4$ and $R_5$, independently of one another, are hydrogen or methyl, wherein a p-substituted phenylpropanol of the formula (IV)

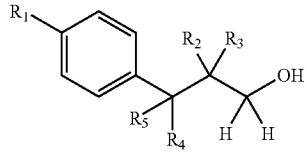
(IV)

in which $R_1$ is $C_1$-$C_5$-alkyl and $R_2$, $R_3$, R4 and $R_5$, independently of one another, are hydrogen or methyl, is isomerized in the presence of a Friedel-Crafts catalyst to give the m-substituted phenylalkanol of the formula (III).

3. The process according to claim 1, wherein the starting compound used is a p-substituted phenylpropanol of the formula (V)

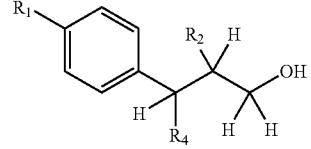
(V)

in which $R_1$ is $C_1$-$C_5$-alkyl and $R_2$ is hydrogen or methyl.

4. The process according to claim 1, wherein the starting compound is a p-substituted phenylpropanol in which $R_1$ is ethyl, isopropyl, isobutyl and tert-butyl.

5. The process according to claim 1, wherein the Friedel-Crafts catalyst used is $AlCl_3$, $AlBr_3$, $TiCl_4$, $ZrCl_4$, $VCl_3$, $ZnCl_2$, $FeBr_3$ or $FeCl_3$.

6. The process according to claim 5, wherein the Friedel-Crafts catalyst used is $AlCl_3$ or $AlBr_3$.

7. The process according to claim 1, wherein the Friedel-Crafts catalyst is used in an amount of from 1 to 200 mol %, based on the molar amount of the p-substituted phenylpropanol used.

8. The process according to claim 1, wherein the isomerization is carried out at a temperature between 0 and 100° C.

9. The process according to claim 1, wherein 2-methyl-3-(4-tert-butylphenyl)propanol is isomerized to give 2-methyl-3-(3-tert-butylphenyl)propanol.

10. The process according to claim 1, wherein the isomerization is carried out starting from 2-methyl-3-(4-isobutylphenyl)propanol, 3-(4-tert-butyl-phenyl)propanol, 2-methyl-3-(4-isopropylphenyl)propanol, 3-(4-ethylphenyl)-2,2-dimethylpropanol or 3-(4-isopropylphenyl)butanol.

11. A process for the preparation of a fragrance of the formula (VI)

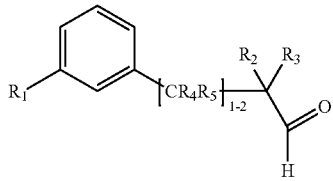
(VI)

in which $R_1$ is $C_1$-$C_5$-alkyl and $R_2$, $R_3$, $R_4$ and $R_5$, independently of one another, are hydrogen or methyl, wherein a p-substituted phenylalkanol of the formula (II)

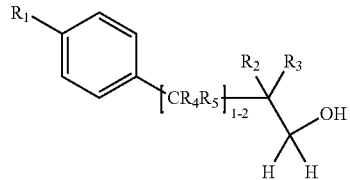
(II)

in which $R_1$, $R_2$, $R_3$, $R_4$ and $R_5$ have the meanings given under formula (VI), is isomerized in the presence of a Friedel-Crafts catalyst to give an m-substituted phenylpropanol of the formula (I)

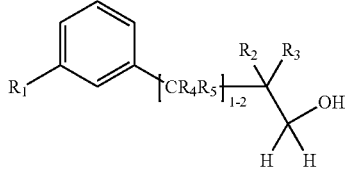
(I)

in which $R_1$, $R_2$, $R_3$, $R_4$ and $R_5$ have the meanings given under formula (II), and then the resulting m-substituted phenylpropanol of the formula (I) is converted to the fragrance of the formula (VI) by oxidation or dehydrogenation.

12. A fragrance or aroma substance of the formula

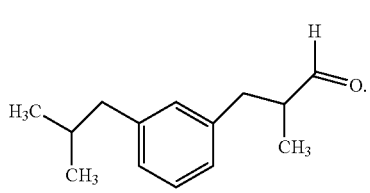
(VII)

13. A formulation which comprises at least one fragrance and aroma substance of the formula (VI)

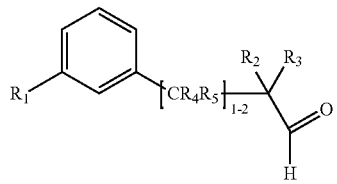
(VI)

in which $R_1$ is $C_1$-$C_5$-alkyl and $R_2$, $R_3$, $R_4$ and $R_5$, independently of one another, are hydrogen or methyl, together with one or more fragrances and aroma substances from the series menthol, tonalide, iso E Super® of the formula (XII)

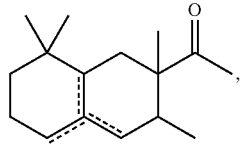
(XII)

galaxolide, ambroxide, citral, linalool, geraniol, methylionone, phenylethyl alcohol, hedione, dihydromyrcenol.

14. The formulation according to claim 13 which comprises the fragrance and aroma substance of the formula (VIII)

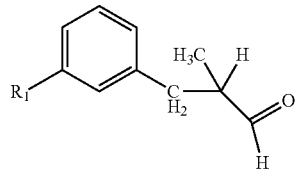
(VIII)

in which $R_1$ is tert-butyl, together with at least one or more fragrances and aroma substances from the series menthol, tonalide, iso E Super® of the formula (XII)

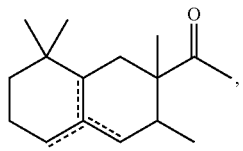
(XII)

galaxolide, ambroxide, citral, linalool, geraniol, methylionone, phenylethyl alcohol, hedione, dihydromyrcenol.

15. The formulation according to claim 13, in which fragrances and aroma substances of the formula (IX)

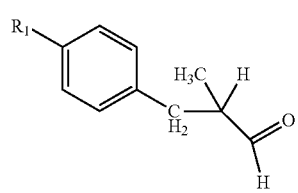
(IX)

in which $R_1$ is tert-butyl, are present in the formulation with a content between 0 and 1000 ppm of the aldehyde of the formula (IX).

16. The formulation according to claim 15, in which the content of the aldehyde of the formula (IX) is 0 ppm.

17. The process according to claim 7, wherein the Friedel-Crafts catalyst is used in an amount between 33 and 110 mol %, based on the molar amount of the p-substituted phenylpropanol used.

* * * * *